US009504600B2

(12) United States Patent
Nielsen

(10) Patent No.: US 9,504,600 B2
(45) Date of Patent: Nov. 29, 2016

(54) UNROLLING STRIPS

(75) Inventor: Henrik Lindenskov Nielsen, Smoerum (DK)

(73) Assignee: Coloplast A/S, Humlebaek (DK)

( * ) Notice: Subject to any disclaimer, the term of this patent is extended or adjusted under 35 U.S.C. 154(b) by 2085 days.

(21) Appl. No.: 11/661,255

(22) PCT Filed: Aug. 29, 2005

(86) PCT No.: PCT/EP2005/054246
§ 371 (c)(1),
(2), (4) Date: Mar. 13, 2008

(87) PCT Pub. No.: WO2006/021591
PCT Pub. Date: Mar. 2, 2006

(65) Prior Publication Data
US 2008/0257360 A1 Oct. 23, 2008

Related U.S. Application Data

(60) Provisional application No. 60/690,893, filed on Jun. 16, 2005.

(30) Foreign Application Priority Data

Aug. 27, 2004 (DK) .................. 2004 01294

(51) Int. Cl.
*A61F 6/04* (2006.01)
*A61F 5/453* (2006.01)
*A47G 25/90* (2006.01)
(52) U.S. Cl.
CPC ............. *A61F 5/453* (2013.01); *A47G 25/905* (2013.01); *A61F 6/04* (2013.01); *A61F 2006/049* (2013.01)

(58) Field of Classification Search
CPC .... A61F 5/453; A61F 6/04; A61F 2006/049; A61F 5/44; A61F 5/451; A61F 6/00; A61F 6/02; A61F 2006/047; A47G 25/905
USPC ........ 128/842, 844, 918, 840; 604/349, 347, 604/351, 354, 355, 356
See application file for complete search history.

(56) References Cited

U.S. PATENT DOCUMENTS 4,475,910 A     10/1984   Conway et al.
4,594,277 A *   6/1986   Galli et al. ................... 428/41.3
(Continued)

FOREIGN PATENT DOCUMENTS

DE     1 026 044       3/1958
FR     2649315     *   7/1989
(Continued)

*Primary Examiner* — Victoria J Hicks
(74) *Attorney, Agent, or Firm* — Coloplast Corp., Coloplast A/S; Nick Baumann

(57) ABSTRACT

A device includes a rolled tubular section and at least two strips rolled together with the tubular section. The strips extend from a rim of the tubular section and are spaced a distance apart from each other, with at least a portion of an inside area of the tubular section provided with an adhesive. When rolled, the adhesive on the inside area of the tubular section contacts at least a part of one of the two strips and the two strips form a path along the tubular section. Each of the two strips has a release layer that is configured to provide each of the two strips with a release value away from the adhesive on the inside of the tubular section of between 15-50 dynes.

18 Claims, 4 Drawing Sheets

(56) References Cited

U.S. PATENT DOCUMENTS

| | | | |
|---|---|---|---|
| 4,865,595 A * | 9/1989 | Heyden | 604/352 |
| 4,972,850 A * | 11/1990 | Broad, Jr. | 128/844 |
| 5,176,666 A | 1/1993 | Convay et al. | |
| 5,334,175 A | 8/1994 | Convay et al. | |
| 5,376,085 A | 12/1994 | Convay et al. | |
| 5,459,879 A * | 10/1995 | Fuchs | 2/161.7 |
| 5,531,725 A * | 7/1996 | Steer | 604/349 |
| 5,779,964 A | 7/1998 | Welch et al. | |
| 2002/0121279 A1 | 9/2002 | Sanchez | |

FOREIGN PATENT DOCUMENTS

| | | |
|---|---|---|
| FR | 2 649 315 | 1/1991 |
| FR | 2649315 A1 * | 1/1991 |
| GB | 2286339 | 8/1995 |
| JP | 7-9317 | 2/1995 |
| JP | 8-252277 | 10/1996 |
| JP | 2000-232988 | 8/2000 |
| WO | WO 93/00054 | 1/1993 |
| WO | WO 03/005940 A1 | 1/2003 |

* cited by examiner

UNROLLING STRIPS

This is a national stage of PCT/EP05/054246 filed Aug. 29, 2005 and published in English, claiming benefit of U.S. provisional application No. 60/690,893, filed Jun. 16, 2005.

FIELD OF THE INVENTION

The present invention relates to unrolling a tubular device by pulling a strip, rolled together with the rolled device.

BACKGROUND

External urinary catheters, also known as urisheaths, are conventionally used in urinary catheter devices for aiding male urinary incontinence and for use in hospitals in connection with treatment and surgery of urethral disorders. Such an external urinary catheter normally comprises a sheath or body portion enclosing the shaft of the penis, and a tip portion that is provided with a comparatively short discharge tube, which via a tube is connected to a urine collection bag that is e.g. fastened to the bed or the leg of the user. Unrolling a sheath correctly on a penis can be very challenging. This procedure is often performed by users with poor dexterity or by hospital staff wearing protective gloves for hygienic reasons. However—it is essential that the sheath be fitted correctly to ensure a leak proof seal between the skin and the sheath. Problems occur if the sheath does not unroll evenly or if the protective gloves stick to the sheath adhesive.

One present solution to this problem is a single strip assisting application of the sheath. However, this strip pulls only on one side of the sheath, which causes uneven roll and is difficult to hold with poor dexterity.

The same type of unrolling problem is experienced with gloves for use in a sterile environment, where application of the glove to the hand, without touching the glove, is paramount to maintaining sterility of the glove. Thus, there is a need for tools improving the correct unrolling.

One attempt to improve unrolling is disclosed in DE 1 026 044, which describes a hollow body, especially a condom, where the two ends of a string is rolled up with the condom. The condom can then be rolled onto the penis by placing the unrolled condom on the penis and pulling the string.

Another somewhat similar solution is provided in FR 2 649 315 which also describe a condom having a flexible unrolling tape where its two ends are rolled up with the condom during production and which is pulled when the condom is to be unrolled onto the penis.

Furthermore does U.S. Pat. No. 4,972,850 disclose a no hands contraceptive device wherein a condom having a rolled portion is provided with a pair of strips. The strips have a width which is sufficiently great to cause the rolled portion of the condom to assume a generally elliptical configuration having a length to width ratio of at least 1.2 to prevent a premature unrolling and the tangling of the condom which may occur when the condom partially enrolls prematurely.

SUMMARY

The solution to the above problems is an element of thin material that allows at least two lengths of it to run in a parallel fashion down either side of the sheath. The two lengths of the element are rolled with the sheath. The top end of the element towards the sheath tip is formed as a loop big enough to grab and pull with a male thumb. When pulling the loop in a downward motion, the sheath is unrolled.

With the double action strip, the sheath is more easily unrolled onto the penis in an even fashion and without having to touch the adhesive.

DETAILED DISCLOSURE

Thus, the present invention relates to a device with a rolled tubular section, the tubular section comprising at least two strips rolled together with the tubular section, the strips placed in suitable distance from each other along the rim of the unrolled tube to ensure unrolling along the rim of the tube in a way that allows the tube to unroll in an even fashion when pulling the strips.

The invention especially relates to a device wherein at least one area of the tubular section is provided with an adhesive and when rolled the at least one area is in contact with at least a part of at least one of the two strips.

The basic problem solved by the invention is that the tubular device now can be unrolled evenly by pulling the strips. Further, it is not needed to touch the device. When unrolling an urisheath with adhesive on the inside, this is particularly important as the nurse is typically wearing gloves, which tend to stick to the adhesive on the urisheath.

Alternatively the nurse may remove the gloves in order to unroll the urisheath, which eases the application of the urisheath. However, this increases the risk of infection, while also invading the intimacy of the patient and the nurse. Thus, by providing a device according to the invention, the nurse can avoid touching the urisheath and the adhesive applied thereto, while keeping the gloves on and thus retaining the barrier against contamination and the intimacy of the patient.

Advantageously the strips can be placed in a suitable distance from each other. Such suitable distance is typically specified by the degree, of which the strips are placed along the rim and calculated by dividing the degree measure of the rim, typically 360° corresponding to the degree number of a circle, with the number of strips. Thus it can be calculated that if two strips are used the suitable distance between the two strips are 180° and if three strips are used the suitable distance would be 120°.

With reference to FIG. 4, a urisheath external urinary catheter 1 includes a rolled tubular section 100 and a discharge tube 102 connected to the rolled tubular section 100, where the discharge tube 102 is attachable at 104 to a urine collection bag. In one embodiment of the invention, at least two strips 4, 5 are joined outside the rolled tubular section 100. This provides for one major advantage of the present invention: for example urisheath users with poor dexterity will now be able to apply the urisheath themselves, without outside help by only using one hand. This is a major break-through to the self-esteem of these users. In a further embodiment joint strips form a handle for unrolling the rolled tubular section. If an even further embodiment the joint strips form a finger-pull-hole 20 (FIG. 5). Such finger-pull-hole 20 enables the user of for example an urisheath to insert a finger, and pull. Whereas an ear handle (FIG. 1) requires two fingers that apply a force between the fingers like a tweezers grip, the finger-pull-hole 20 only requires a pull force.

In a typical aspect of the invention, the tubular section rolls outwards. This is the classic formation of for example condoms and urisheaths.

However, in a special embodiment the tubular section rolls inwards. In this embodiment it is preferred that the strips are pulled out of the rolled tubular section, and thereby allow an inside-out unrolling.

One overall type of devices with a rolled tubular section is bags for something that is desired to be compressed. That is, the bag has a volume that approximately fits the compressed contents. An example thereof is a device selected from the group consisting of a tent bag and a sleeping bag cover. Having rolled the sleeping bag, the rolled sleeping bag cover is positioned at the end of the rolled sleeping bag. Pulling the at least two strips of the sleeping bag cover will unroll the sleeping bag cover onto the sleeping bag, and will at the same time compress the sleeping bag. The same applies to the tent bag and other similar devices in the group.

Another overall type of devices with a rolled tubular section is a device with flexible/elastic properties to fit closely to something. That is a device with a sphere slightly smaller than the intended contents, but due to the flexible and/or elastic properties of the material it will fit the contents. An example thereof is a device selected from the group consisting of socks, stocking, condoms and urisheaths. Having for example a foot, the rolled sock is placed at the tip of the toes. Pulling the at least two strips of the sock will unroll the sock onto the foot. The flexibility of the material of the sock will ensure that the sock stays in place after placement. The same applies to the condoms, urisheaths and other similar devices in the group.

A special overall type of devices with a rolled tubular section with at least two strips is a device that shall not be touched during application, unrolling and/or use. An example of such device is a device used for sterile procedures, such as sterile gloves. Rolling a sterilized glove with at least two strips, will enable application of the glove by putting one hand into the rolled glove, and pulling the two strips with the other hand—or by placing the handle of the two strips on a rod-like structure, and pushing the glove on. Hereby, the glove is positioned on the hand without touching it. In a similar way, the urisheath with two strips is applied by pulling the two strips, as opposed to the usual manual unrolling. Hereby is obtained that the urisheath, more specifically the adhesive, is untouched when applied to the penis. Not only will this secure optimal adhesiveness to the penis, it also alleviates the problem experienced by the nurse, when her gloves adhere to the urisheath during application.

In one aspect of the invention, it is preferred that the tubular section is thin-walled.

The strips used with urisheaths are made of the least material needed to obtain the required force without material extension or breaking, and are preferably made of polyethylene.

As the sheath comprises an adhesive layer 30 (FIG. 2), the strips 4, 5 preferably comprise a release layer 32 to avoid adhesion to the adhesive layer 32 on the inside of the urisheath.

To obtain the desired performance of the strip to un-roll the urisheath onto the penis, a strip material with sufficient release from the sheath adhesive has to be used. One embodiment of a strip material could be a polyolfin film such as polyethylene or polypropylene coated with a silicone with a release value from the urisheath of 20-30 dyne. In some cases, when the choice of materials and adhesives allow, an un-coated polyolifin film with a higher release value will provide sufficient release of the adhesive in order for the sheath to un-roll.

As it can be understood different materials used for the urisheath and the release liner for the strips can provide different dyne values. However, without limiting the invention it can be generally understood that strip materials causing a release force from the urisheah with a dyne value above 50 dyne rarely will be used, as this would generate an exaggerated pull during application of the urisheath. Thus in one embodiment of the invention the dyne value between the tubular section and each of the at least two strips is between 15-50 dyne, especially between 20-40 dyne and particularly between 20-30 dyne.

In preparation of the rolled tubular section, the strips will typically be applied in the unrolled condition. Thereafter, the tubular section is rolled, so that the strips 4, 5 are placed in between the inside and outside of the tube. Hereby each of the strips 4, 5 forms a path P (FIG. 3) along the tubular section.

In one embodiment, each of those paths is parallel to longitudinal axis L (FIG. 3) of the unrolled tubular section-hereby securing an even draw.

However, when placing the strips 4, 5 (FIG. 3) parallel to the longitudinal axis L of the unrolled section, the rolled tubular section will have an un-even outer rim, thicker where the strips are, thinner at places along the rim, where the strips are absent. In order to obtain a smoother surface of the rolled tubular section, at least one path formed by the strips 4', 5' (FIG. 5) is a spiral shape S.

The exact position of the strips, the length extending outside of the rolled tubular section and their optional point of joining, depends on a number of factors. Some of the scenarios described below will illustrate this:

In the design of a sleeping bag cover, three or even four or five strips would be considered appropriate to ensure the force needed to compress the sleeping bag during unrolling the sleeping bag cover. Even unrolling is important to ensure sufficient compression of the material. In this case the strips would be joined over the center of the tube, i.e. is over the center of the sleeping bag cover. Each of the three strips would be spaced evenly along the rim of the rolled tube, that is at 0° (e.g. vertical to the right), 120° and 240°. Each of the strips would likewise be placed evenly along the rim of the rolled tube that is at 0°, 90°, 180° and at 270°. In use, the rolled sleeping bag is placed on top of the rolled sleeping bag cover inside the net of strips. Pushing the sleeping bag against the sleeping bag cover, and at the same time pulling the strips will unroll the sleeping bag cover on top of the sleeping bag.

Typically in the design of an urisheath, two strips are sufficient. The number of strips is determined as a balance between the importance of even rolling, then countered by the increased production complexity and the chance of tangling the strips during use. In this case the strips are joined along the rim of the rolled section. Taking this point on the rim as 0°, the first strip is placed at −90°, and the second strip is placed at +90°, hereby distributing the strips evenly along the rim with equally long strips. However, in another embodiment, the handle, where the strips are joined, is not centered between the two points. Thus, the first strip is placed at 0°, and the other strip at 180°, and consequently the part of the first strip extending outside of the rolled tubular device is shorter than part of the second strip extending outside of the rolled tubular device. Similar considerations apply when the placement of the (first strip, second strip) are (−2°, 178°), (−4°, 176°), (−6°, 174°), (−8°, 172°), (−10°, 170°), (−12°, 168°), (−14°, 166°), (−16°, 164°), (−18°, 162°), (−20°, 160°), (−22°, 158°), (−24°, 156°), (−26°, 154°), (−28°, 152°), (−30°, 150°), (−32°, 148°), (−34°, 146°), (−36°, 144°), (−38°, 142°), (−40°, 140°), (−42°, 138°), (−44°, 136°), (−46°, 134°), (−48°, 132°), (−50°, 130°), (−52°, 128°), (−54°, 126°), (−56°, 124°), (−58°, 122°), (−60°, 120°), (−62°, 118°), (−64°, 116°), (−66°, 114°), (−68°, 112°), (−70°, 110°), (−72°, 108°), (−74°, 106°), (−76°, 104°), (−78°, 102°), (−80°, 100°), (−82°, 98°), (−84°, 96°), (−86°, 94°), (−88°, 92°), (−90°, 90°), (−92', 88°), (−94°, 86°), (−96°, 84°), (−98°, 82°), (−100°, 80°), (−102°, 78°), (−104°, 76°), (−106°, 74°), (−108°, 72°), (−110°, 70°), (−112°, 68°), (−114°, 66°), (−116°, 64°), (−118°, 62°), (−120°, 60°), (−122°, 58°), (−124°, 56°), (−126°, 54°), (−128°, 52°), (−130°, 50°), (−132°, 48°), (−134°, 46°), (−136°, 44°), (−138°, 42°), (−140°, 40°), (−142°, 38°), (−144°, 36°), (−146°, 34°), (−148°, 32°), (−150°, 30°), (−152°, 28°), (−154°, 26°), (−156°, 24°), (−158°, 22°), (−160°, 20°), (−162°, 18°), (−164°, 16°), (−166°, 14°), (−168°, 12°), (−170°, 10°), (−172°, 8°), (−174°, 6°), (−176°, 4°), (−178°, 2°), or (−180°, 0°).

It is noted that it is not required that the strips are distributed evenly along the rim of the tubular device. For example, if the obstacles the strips are passing to join coming from diagonal sides, and the stiffness of the tubular section material allows it, the strips are spaced with an angle lower than 180°, such as 178°, 176°, 174°, 172°, 170°, 168°, 166°, 164°, 162°, 160°, 158°, 156°, 154°, 152°, 150°, 148°, 146°, 144°, 142°, 140°, 138°, 136°, 134°, 132°, 130°, 128°, 126°, 124°, 122°, 120°, 118°, 116°, 114°, 112°, 110°, 108°, 106°, 104°, 102°, 100°, 98°, 96°, 94°, 92°, 90°, 88°, 86°, 84°, 82°, or even 80°.

The same considerations apply when using three or more strips.

Manufacturing of the tubular section as described herein, is typically quite simple. It comprises the steps of
(a) adding before rolling, at least two strips in suitable distance from each other along the rim of the tube.
(b) rolling the tubular section in a way that the strips are rolled together with the tubular section.

Likewise, a method for unrolling a device with a rolled tubular section, the tubular section comprising at least two strips rolled together with the tubular section, the strips placed in suitable distance from each other along the rim of the unrolled tube to ensure unrolling along the rim of the tube in a way that allows the tube to unroll in an even fashion when pulling the strips comprises pulling the strips in an angle between parallel to the longitudinal axis away from the tip and perpendicular to the longitudinal axis at the point of the rolled tubular section.

EXAMPLES

Example 1

Comparison Between 1 and Two Strips

Figure 1:
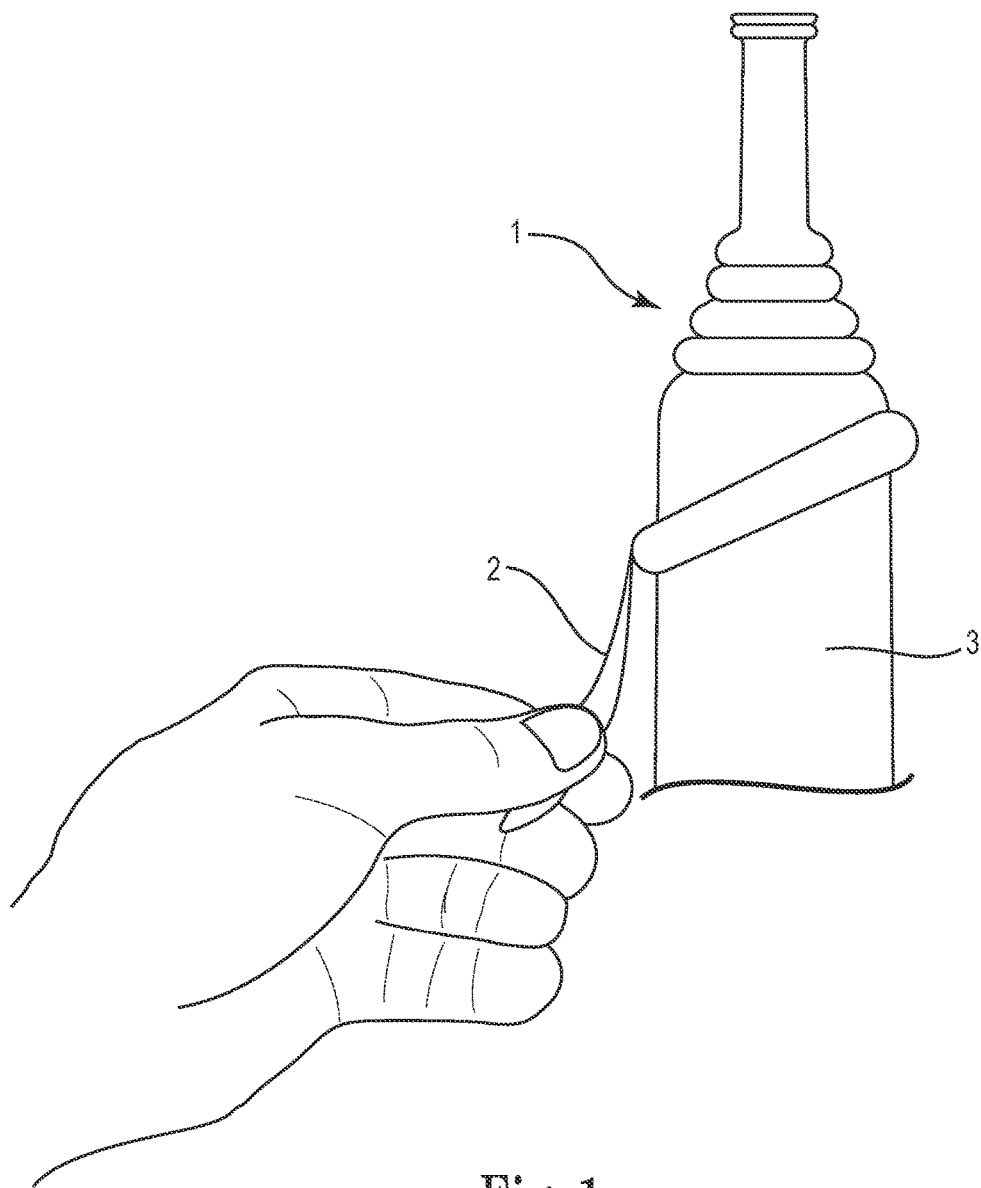
FIG. 1: Application of a prior art urisheath with one strip.

A regular urisheath 1 with one strip 2 was applied to a penis dummy 3. As illustrated in FIG. 1, when pulling the strip, the urisheath will be drawn down unequally.

Figure 2:
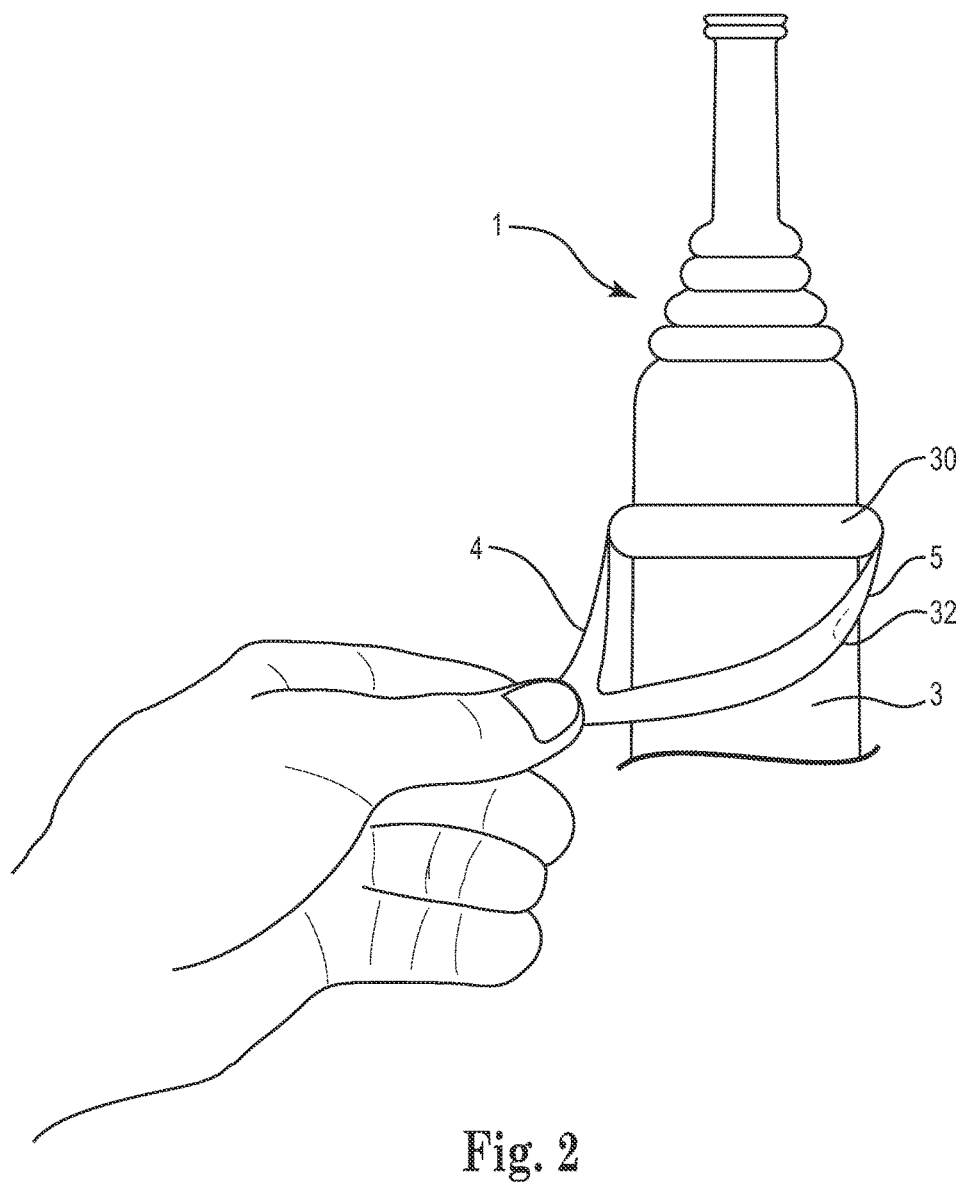
FIG. 2: Application of urisheath with two strips.
Figure 3:
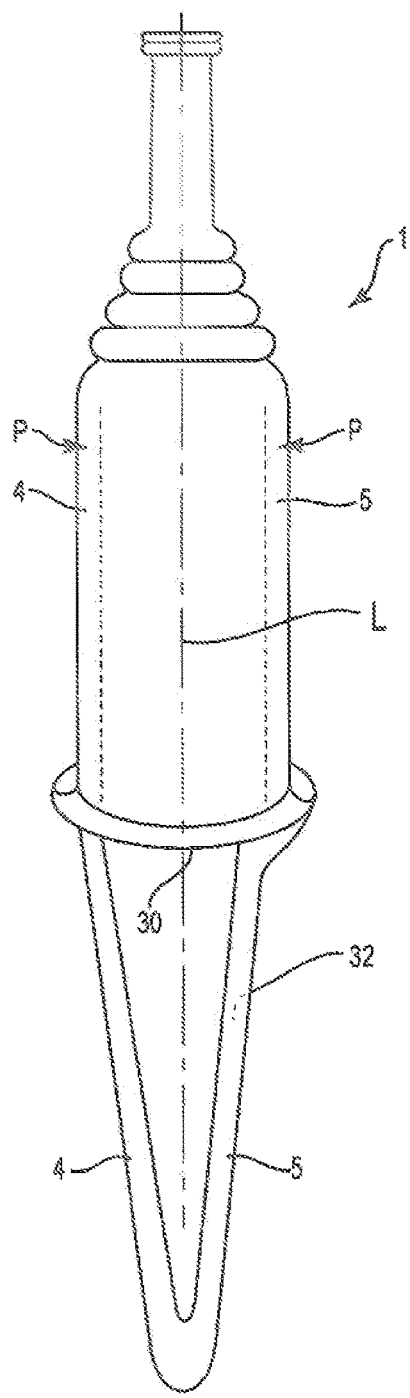
FIG. 3: Front plan view of unrolling the urisheath illustrated in FIG. 2.
Figure 4:
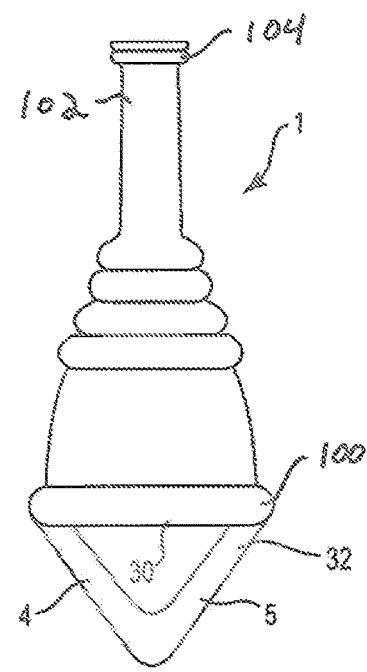
FIG. 4: Front plan view of the urisheath illustrated in FIG. 2 in a rolled configuration.
Figure 5:
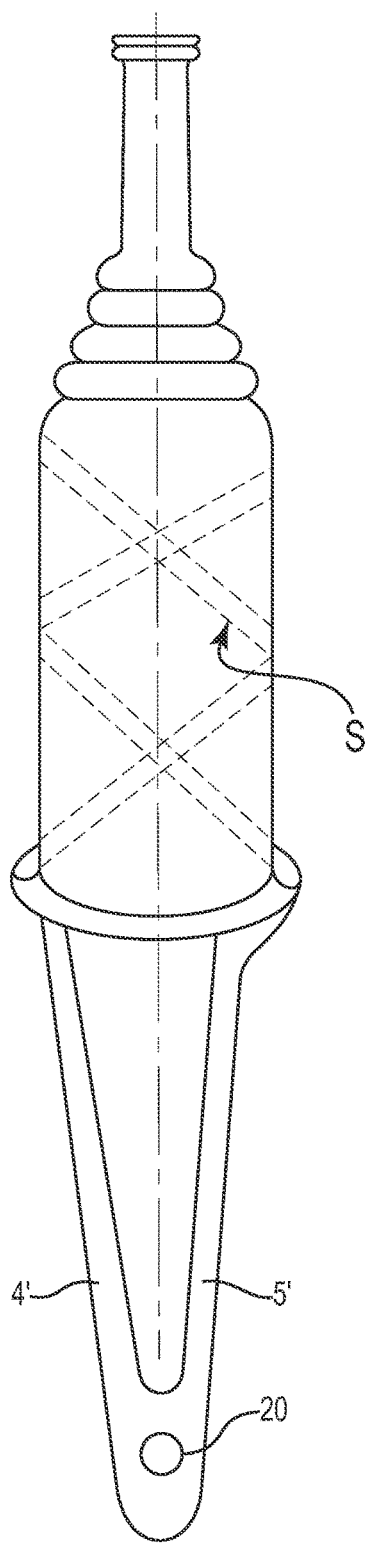
FIG. 5: Front plan view if a urisheath including strips in a spiral pattern.

In another experiment, a regular urisheath 1 with two strips 4,5 was applied to a penis dummy 3. As illustrated in FIG. 2, this urisheath is pulled downward equally along the rim of the sheath. Thus, it can be understood that by providing two strips the force applied to the urisheath when pulling, is distributed at two points. This provides for a more uniform application of the urisheath. As mentioned earlier more than two strips can be used in order to distribute the pulling force more evenly.

The invention claimed is:

1. A device comprising:
an external urinary catheter comprising a rolled tubular section and a discharge tube connected to the rolled tubular section, the discharge tube attachable to a urine collection bag, and the rolled tubular section including at least two strips rolled together with the rolled tubular section, the at least two strips extending from a rim of the rolled tubular section and spaced a distance apart from each other, with at least a portion of an inside area of the rolled tubular section provided with an adhesive that contacts at least a part of the at least two strips that are rolled together with the rolled tubular section;
wherein the at least two strips are configured to release from the adhesive on the inside of the rolled tubular section when the at least two strips are pulled to thus unroll the rolled tubular section over a penis and allow the adhesive on the inside area of the rolled tubular section to secure the external urinary catheter to the penis.

2. The device of claim 1, wherein the at least two strips are joined to each other outside of the rolled tubular section to define a joined strip.

3. The device of claim 2, wherein the joined strip forms a handle for unrolling the rolled tubular section.

4. The device of claim 3, wherein the handle defines a finger-pull-hole.

5. The device of claim 1, wherein the at least two strips form a path along the rolled tubular section.

6. The device of claim 5, wherein the rolled tubular section defines a longitudinal axis when unrolled and the path is parallel to the longitudinal axis.

7. The device of claim 5, wherein the path is a spiral-shaped path.

8. The device of claim 1, wherein the at least two strips are formed of polyethylene.

9. The device of claim 1, wherein the at least two strips are formed of polypropylene.

10. An external urinary catheter comprising:
a discharge tube connected to a tubular section, the discharge tube attachable to a urine collection bag;
the tubular section including adhesive on an inside portion of the tubular section to secure the external urinary catheter to a penis; and
two strips on the tubular section;
wherein the tubular section is rolled to provide a rolled tubular section, at least a part of the two strips are rolled together with the rolled tubular section, and another part of the two strips extend from a rim of the rolled tubular section;
wherein the two strips are configured to release from the adhesive of the tubular section.

11. The external urinary catheter of claim 10, wherein the two strips form a path along the rolled tubular section.

12. The external urinary catheter of claim 11, wherein the rolled tubular section defines a longitudinal axis when unrolled and the path is parallel to the longitudinal axis.

13. The external urinary catheter of claim 11, wherein the path is a spiral-shaped path.

14. The external urinary catheter of claim 10, wherein the two strips are configured to allow the rolled tubular section to unroll evenly.

15. The external urinary catheter of claim 10, wherein the two strips are joined together to form a finger-pull-hole.

16. The external urinary catheter of claim 10, wherein the two strips are spaced a distance apart from each other.

17. The external urinary catheter of claim 10, wherein the two strips are formed of polyethylene.

18. An external urinary catheter comprising:
   a discharge tube connected to a tubular section, the discharge tube attachable to a urine collection bag;
   the tubular section including adhesive on an inside portion of the tubular section for adhesive attachment of the external urinary catheter to
   two strips on the tubular section;
   wherein the tubular section is rolled to provide a rolled tubular section, with a first part of each of the two strips rolled together with the rolled tubular section to thus locate the first part of the two strips between an inside and an outside of the rolled tubular section, and a second part of each of the two strips extending away from the rolled tubular section;
   wherein the two strips release from the adhesive of the tubular section when the rolled tubular section is unrolled and the external urinary catheter is able to be adhesively attached to a penis.

\* \* \* \* \*